US006080579A

United States Patent [19]
Hanley, Jr. et al.

[11] Patent Number: 6,080,579
[45] Date of Patent: *Jun. 27, 2000

[54] METHOD FOR PRODUCING HUMAN INTERVERTEBRAL DISC CELLS

[75] Inventors: Edward Nathaniel Hanley, Jr.; Helen Elizabeth Gruber, both of Charlotte, N.C.

[73] Assignee: Charlotte-Mecklenburg Hospital Authority, Charlotte, N.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/979,674

[22] Filed: Nov. 26, 1997

[51] Int. Cl.$^7$ .............................. C12N 5/00; C12N 5/08
[52] U.S. Cl. ..................... 435/366; 435/378; 435/379; 435/382; 435/395; 435/399
[58] Field of Search ......................... 424/93.7; 435/325, 435/366, 372, 382, 384, 387, 392, 395, 399, 347, 378, 379

[56] References Cited

U.S. PATENT DOCUMENTS

| | | | |
|---|---|---|---|
| 4,485,097 | 11/1984 | Bell .......................................... | 424/549 |
| 5,032,508 | 7/1991 | Naughton et al. ......................... | 435/32 |
| 5,155,034 | 10/1992 | Wolf et al. ................................ | 435/402 |
| 5,256,418 | 10/1993 | Kemp et al. .............................. | 424/423 |
| 5,266,476 | 11/1993 | Sussman et al. .......................... | 435/399 |
| 5,422,340 | 6/1995 | Ammann et al. .......................... | 514/12 |
| 5,496,722 | 3/1996 | Goodwin et al. ......................... | 435/371 |
| 5,585,116 | 12/1996 | Boniface et al. ......................... | 424/549 |

OTHER PUBLICATIONS

Martin, in Tissue Culture, Methods and Applications, Ed., P.F. Kruse, Jr., and M.K. Patterson, Jr., Academic Press, NY, Chapter 1, pp. 39–43, 1973.
Malemud et al., Matrix, 12:427–438, 1992.
Aulthouse et al., In Vitro Cell. Develop. Biol., 25:659–668, 1989.
Wang et al. in Chemistry and Biology of Mineralized Tissues, ed. H. Slavkin and P. Price, Elsevier Science Publishers B.V., pp. 351–359, 1992.
Gruber et al., Exp. Cell Research, 235:13–21, 1997.
Maurer, in Animal Cell Culture, A Practical Approach, ed. RI Freshney, IRL Press, pp. 13–31, and 150–151, 1987.
Osada et al. Journal of Orthopaedic Research, 14:690–699, 1996.
Paul D. Benya, et al., Dedifferentiated Chondrocytes Reexpress The Differentiated Collagen Phenotype When Cultured In Agarose Gels, *Cell*, vol. 30, Aug. 1982, pp. 215–224.
Jinfeng Guo, et al., Culture And Growth Characteristics Of Chond4rocytes Encapsulated In Alginate Beads, *Connective Tissue Research*, vol. 19, 1989, pp. 277–297.
J. Paul Thompson, et al., Stimulation Of Mature Canine Intervertebral Disc By Growth Factors, *Spine*, vol. 16, No. 2, 1991, pp. 253–260.
Brian A. Maldonado, et al., Initial Characterization Of The Metabolism Of Intervertebral Disc Cells Encapsulated In Microspheres, *Journal of Orthopaedic Research*, vol. 10, pp. 677–690.
J. Bonaventure, et al., Reexpression Of Cartilage–Specific Genes By Dedifferentiated Human Articular Chondrocytes Cultured In Alginate Beads, *Experimental Cell Research*, vol. 212, 1994, pp. 97–104.
Mary K. Chelberg, et al., Identification Of Heterogeneous Cell Populations In Normal Human Intervertebral Disc, *J. Anat.*, vol. 186, Accepted Jul. 6, 1994, pp. 43–53.
Steven L. Frick, et al., Lumbar Intervertebral Disc Transfer—A Canine Study, *Spine*, vol. 19, No. 16, Aug. 15, 1994, pp. 1826–1835.
Akitomo Katsuura, et al., Experimental Study Of Intervertebral Disc Allografting In The Dog, *Spine*, vol. 19, No. 21, Nov. 1, 1994, pp. 2426–2432.
Job L. C. van Susante, et al., Culture Of Chondrocytes In Alginate And Collagen Carrier Gels, *Acta Orthop Scand*, vol. 66, No. 6, 1995, pp. 549–556.
C. Frondoza, et al., Human Chondrocytes Proliferate And Producce Matirx Components In Microcarrier Suspension Culture, *Biomaterials*, vol. 17, 1996, pp. 879–888.
Hiromi Matsuzaki, et al., Allografting Intervertebral Discs In Dogs—A Possible Clinical Application, *Spine*, vol. 21, No. 2, Jan. 15, 1996, pp. 178–183.
Kjell Olmarker, et al., Ultrastructural Changes In Spinal Nerve Roots Induced By Autologous Nucleas Pulposus, *Spine*, vol. 21, No. 4, Feb. 15, 1996, pp. 411–414.
Transforming Growth Factor–$\beta 1$ (TGF–$\beta$) Regulates Proliferation and Proteoglycan Gene Expression in Diseased Human Intervertebral Disc Cells, H.E. Gruber et al., J. Bone Mineral Res: 11 (suppl.1):s300, 1996.

*Primary Examiner*—Jon P. Weber
*Assistant Examiner*—Janet M Kerr
*Attorney, Agent, or Firm*—Alston & Bird LLP

[57] ABSTRACT

There is provided a method for growing human intervertebral cells. Disc tissue is surgically removed from a normal disc of a patient, the cells expanded by feeding with a cell stimulant such as a growth factor, or a cytokine or a bioactive agent to form monolayer primary cell cultures on a plastic mesh such as a nylon mesh. In the case of a growth factor, fetal bovine serum is preferred as it improves cell proliferation and production of appropriate extracellular matrix components. In another aspect of this invention, the monolayer primary cell cultures are seeded in alginate or agarose and fed again with the cell stimulant until three-dimensional cell cultures are formed. The cells are recovered from the alginate or agarose or from monolayer cultures. Re-implantation is carried out using bioresorbable carriers or cell suspensions.

11 Claims, 5 Drawing Sheets

(3 of 5 Drawing Sheet(s) Filed in Color)

Type I Collagen

Type II Collagen

Type III Collagen

Type VI Collagen

4-S-Chondroitin Sulfate

Keratan Sulfate

1

METHOD FOR PRODUCING HUMAN INTERVERTEBRAL DISC CELLS

BACKGROUND OF THE INVENTION

This invention relates to a method for producing human intervertebral disc cells. More particularity, this invention relates to methods for growing intervertebral cells in monolayers cultures followed by three-dimensional growth of cells.

In spite of the large health care costs associated with degenerative disc disease, the cell biology of the human intervertebral disc cell has been neglected compared to the knowledge available on chondrocytes or bone cell populations. Recent studies have presented data on the formation and turnover of matrix in situ in the human disc. Antoniou, J., Steffen, T., Nelson, F., Winterbottom, N., Hollander, A. P., Poole, R. A., Aebi, M., Alini, M., "The human lumbar intervertebral disc-Evidence for changes in the biosynthesis and denaturation of the extra cellular matrix with growth, maturation, ageing, and degeneration," *J. Clin. Invest.* 98, 996–1003 (1996). Growth of the young disc showed active matrix formation and denaturation of Type II collagen; aging and maturation were associated with decreased matrix synthesis and reduced denaturation of Type II collagen. Degenerative stages showed decreased aggrecan and Type II procollagen formation and increased Type II denaturation and Type I collagen synthesis. Successful isolation and in vitro growth of disc cells under experimental conditions can be a valuable tool for clarification of the cellular mechanisms involved in these observed matrix changes.

Studies of human disc cells cultured in alginate beads have provided evidence that more than one distinctive cell population resides in the disc. Chelberg, M. K., Banks, G. M., Geiger, D. F., Oegema, T. R., "Identification of heterogeneous cell populations in normal human intervertebral disc," *J Anat*, 186, 43–53 (1995). Others have used the alginate bead technique to study canine disc cells in culture. Maldonado, B. A., Oegema, T. R., "Initial characterization of the metabolism of intervertebral disc cells encapsulated in microspheres," *J Orthopaedic Res,* 10, 677–690 (1992). Cells from the rat disc have been grown in monolayer culture. Ichimura, K., Tsuji, H., Matsui, H., Makiyama, N., Cell culture of the intervertebral disc of rats: Factors influencing culture, proteoglycan, collagen, and deoxyribonucleic acid synthesis," *J Spinal Disorders,* 4, 428–436 (1991).

Three-dimensional cell culture is a preferred culture method for chondrocytes, a cell type similar to at least some members of the disc cell population, and is known to de-differentiate in monolayer culture and reexpress a characteristic Type II collagen extracellular matrix production when placed in agarose culture. Benya, P. D., Shaffer, J. D., "Dedifferentiated chondrocytes reexpress the differentiated collagen phenotype when cultures in agarose gels," *Cell,* 30, 215–224 (1982).

It is an object of the present invention to produce human intervertebral cells in monolayer explant cultures.

Another object of the present invention is to produce human intervertebral cells in a three-dimensional cultures.

SUMMARY OF THE INVENTION

It has been found the human intervertebral cells may be grown and implanted into individuals with idiopathic scoliosis, herniated disc, degenerative disc disease, recurrent disc herniation or spinal stenosis. Healthy specimens are obtained from the patient by either direct or percutaneous routes by a physician.

In a first embodiment of the present invention intervertebral healthy cells from a patient are grown into primary cell cultures in the presence of a cell stimulant such as a growth factor, or a cytokine or a bioactive agent to form monolayer primary cell cultures. In the case of a growth factor, fetal bovine serum is preferred as it improves cell proliferation and production of appropriate extracellular matrix components. The explant is first preferably grown on a nylon mesh anchor which simplifies feeding; cell are then expanded to larger numbers in monolayer culture.

In a second embodiment, the monolayer primary cell cultures may be seeded into alginate or agarose and fed again with the cell stimulant until three-dimensional cell cultures are formed. The cells are recovered from the alginate or agarose. Re-implantation into a site of disc degeneration is carried out using bioresorbable carriers or by placing cells directly in a disc.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Figure 1:
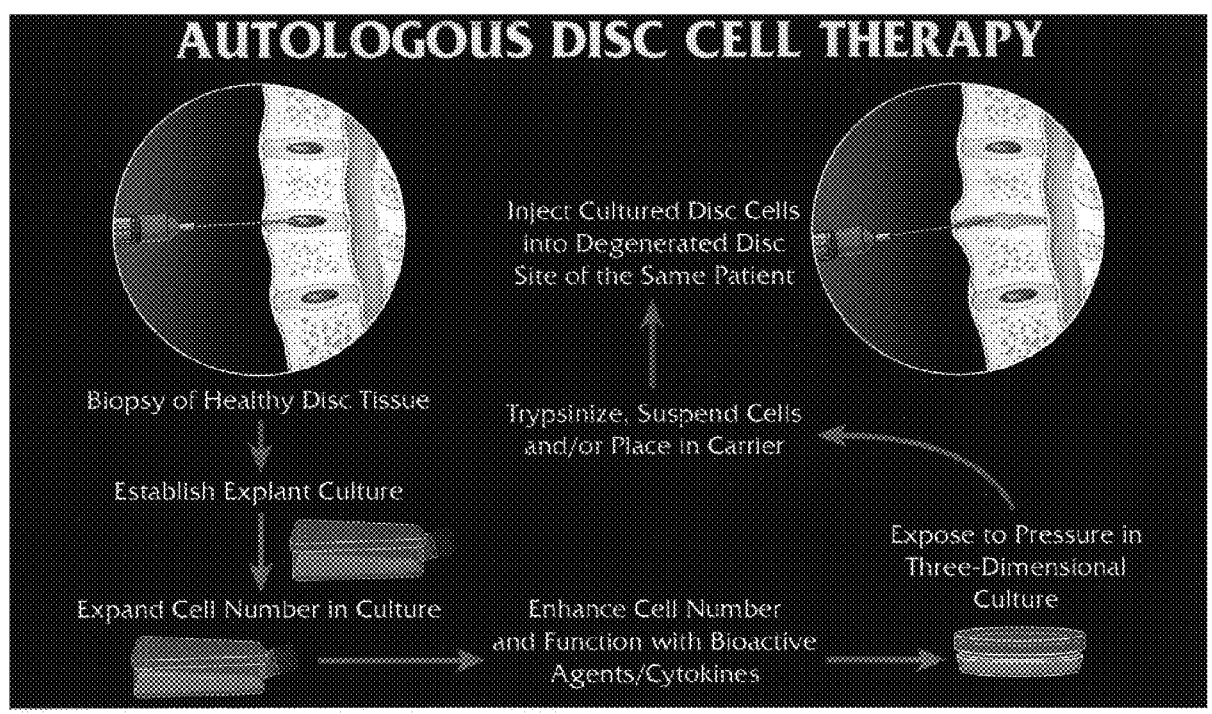
FIG. 1 is a schematic illustration of the process of the present invention.

The present invention is directed to a method for producing human intervertebral cells which are intended for implantation into a patient. It is important that the cells implanted into the patient be grown from the patient's own cells. The present invention in one embodiment provides growing intervertebral cells by feeding with a cell stimulant or merely using an expanded number of cells from monolayer explant culture (primary culture). In another embodiment, this invention provides seeding cells from the primary culture into three-dimensional growth environments of alginate or agarose and continued feeding or without with a cell stimulant. As shown in FIG. 1, disc tissue is surgically removed from a normal disc of a patient, the cells expanded by feeding with a cell stimulant on a plastic mesh such as a nylon mesh, grown in a three-dimensional microenvironment with cell stimulants such as growth factors and bioactive agents to re-express phenotype, placed in a carrier material or injected as a cell suspension and inserted into a site with disc degeneration in that same patient.

Production Of a Monolayer Culture (Primary Culture)

Disc tissue is derived from surgical disc procedures performed on individuals with idiopathic scoliosis, herniated disc, degenerative disc disease, recurrent disc herniation or spinal stenosis and the like. Healthy disc tissue may be obtained by any of the known surgical procedures and placed in a sterile medium and incubated with fungizone as a precaution against contamination. The healthy disc tissue is rinsed with phosphate buffered saline. Regions of annulus and nucleus are visually identified and representative pieces of annulus and nucleus are dissected. Those designated for culturing cells are further examined and any cartilaginous or vascular regions are carefully removed. The disc tissue to be cultured is minced into 1–2 mm square pieces, again rinsed with saline to remove clots or residual debris, placed into culture dishes and anchored by placement of a sterile nylon mesh over the minced explant. Use of the nylon mesh anchoring technique for explants not only simplifies the feeding of cultures by anchoring fragments and thus preventing loss of fragments during cell feeding, but also provides a substrate for cell outgrowth.

To the designated cells is added Minimal Essential Medium (MEM, GIBCO) with Earle's salts, 1% L-glutamine, 1% non-essential amino acids, 1% penicillin-streptomycin and about 20% (v/v) of a cell stimulant, such as a growth factor, or a cytokine or a bioactive agent. Fetal calf serum and fetal bovine serum (GIBCO, Grand Island, N.Y.) are preferred. Other cell stimulants include, for example, transforming growth factor beta (TGF-$\beta$), insulin-like growth factor I, insulin-like growth factor II, basic fibroblast growth factor, acidic fibroblast growth factor, platelet-derived growth factor, serum, insulin, human recombinant bone morphogenetic protein 2, Vitamin D, 1,25-dihydroxyvitamin D, and other forms of bone morphogenetic protein or ITS (insulin-transferrin-selenium). Serum may or may not be present during feeding with the cell stimulant. Cells may also be grown in the Hams medium with addition of previously mentioned agents.

The primary cultures are grown at a temperature between about 30° C. and about 50° C., preferably at 37° C. Normally, the primary cultures are grown at high humidity conditions under a blanket of $CO_2$. These cultures are fed with the cell stimulant every two days. When primary cultures show a confluent outgrowth of cells from the nylon mesh, the cultures are trypsinized. It has been found that cell viability may average 96% on a monolayer culture.

Three-Dimensional Cell Growth

Following trypsinization, cells established in monolayer primary cultures may be seeded in alginate or agarose. Trypsinized cell cultures are assayed for cell viability and the required volume of cell suspension centrifuged and the medium aspirated off.

Regarding alginate, an alginate solution may be prepared by mixing a 1.2% solution of KELTONE LV alginate (KELCO, San Diego, Calif.) in 0.9% physiological saline and then sterilized. An appropriate volume of the sterile alginate solution is added to attain the desired cell/alginate suspension.

The three-dimensional cell structures are grown in multiwell plates. Inserts are placed in the bottom of each well. One type of insert that may be used is a COSTAR TRANSWELL Clear Insert (COSTAR, Cambridge, Mass.). The alginate/cell suspension is added to the insert.

After the alginate/cell suspension is in place, a polymerizing solution is added to the well. The polymerizing solution may be one having a divalent cation. A preferred polymerizing solution is $CaCl_2$. The alginate/cell suspension is incubated in the polymerizing solution for four minutes and the solution aspirated out. Wells were rinsed with MEM with 20% FBS. The rinsing volume is allowed to stand for one minute, aspirated off, and the wells filled with MEM and cell stimulant (as described above) and regularly fed. Methods for disc cell growth in alginate are a modification of the methods described in Maldonado, B. A., Oegema, T. R., "Initial characterization of the metabolism of intervertebral disc cells encapsulated in microspheres," *J Orthopaedic Res*, 10, 677–690 (1992) and Guo, J., Jourdian, G. W., MacCallum, D. K., "Culture and growth characteristics of chondrocytes encapsulated in alginate beads," *Conn Tiss Res* 19:227–297 (1989).

The cells are recovered from alginate by rinsing with NaCl followed by addition of a dissolving buffer, incubated until the alginate is dissolved, centrifuged and rinsed again with NaCl. Cells are similarly recovered from agarose and other carrier types, as required. These cells, grown in this manner, may be implanted into the patient's disc using sterile, surgical direct or percutaneous techniques with placement of cells or cells on their carriers into regions selected by the surgeon. This may or may not be preceded by direct or percutaneous debridement of diseased tissue areas. Methods for re-implantation into the disc include, but are not limited to, use of cells in alginate, bioresorbable collagen substrates, and other resorbable carriers.

EXAMPLE 1

This example illustrates the growth of healthy disc cultures. Healthy disc tissue was obtained and rinsed with phosphate buffered saline at pH 7.4. The tissue was placed in modified Minimal Essential Medium (MEM) with Earle's salts (MEM, GIBCO, Grand Island, N.Y.) with 1% (v/v) L-glutamine (Irvine Scientific, Santa Ana, Calif.), 1%. (v/v) penicillin-streptomycin (Irvine Scientific, Santa Ana, Calif.), but without added serum. The disc tissue was incubated in three 15-minute rinses of MEM with 1% fungizone (Irvine Scientific) as a precaution against contamination of the cells during removal.

Regions of annulus and nucleus were visually identified and representative pieces of annulus and nucleus were dissected. Cartilaginous and vascular regions removed from tissue designated for culturing. The disc tissue to be cultured was minced with a scalpel into 1–2 mm square pieces, again rinsed twice with saline to remove clots or residual debris, placed into 35 mm culture dishes and anchored by placement of a sterile nylon mesh (SPECTRA MESH, Spectra Laboratory Products) over the minced explant to provide a substrate for cell outgrowth.

A series of cultures were fed with varying amounts of cell stimulant. Minimal Essential Medium (MEM, GIBCO) with Earle's salts and about 20% (v/v) of fetal bovine serum (FBS, GIBCO, Grand Island, N.Y.) was added to the minced explant. The primary cultures were grown at a temperature of 37° C. and 95% humidity under a blanket of 5% $CO_2$. The primary cultures are fed with fetal bovine serum every two days.

Figure 2A:
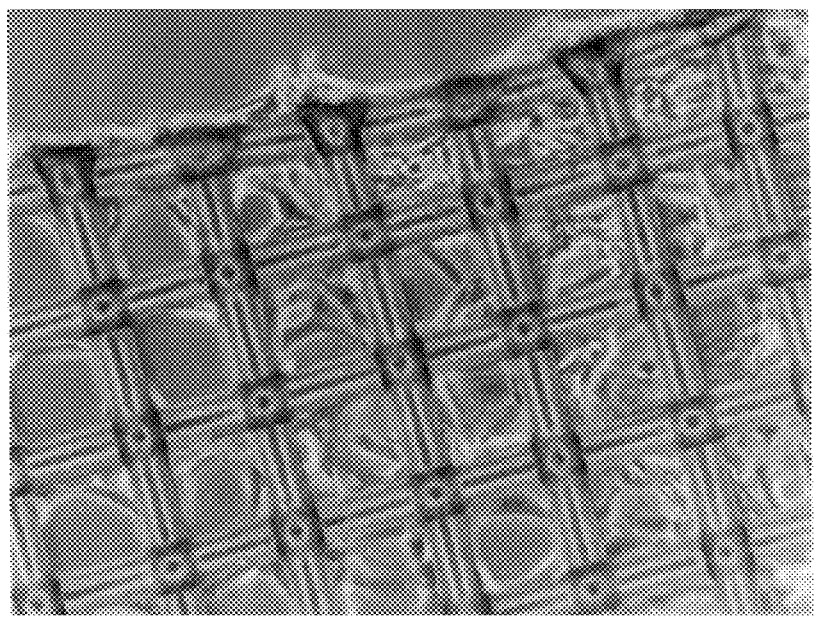
FIG. 2A is a phase-contrast photomicrograph of cells growing from a disc explant fragment onto a nylon mesh (X130)
Figure 2B:
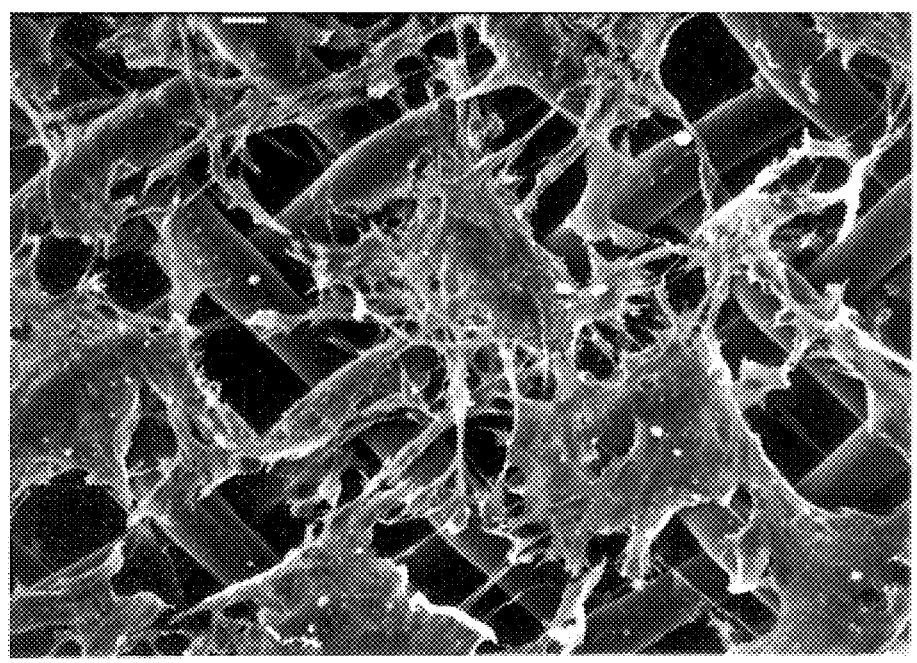
FIG. 2B is a scanning electron micrograph of cells spreading and extending processes onto the mesh (bar at the upper left, 10 μm)

Disc cells from both the annulus and nucleus grew well on the mesh lattice. Cells from the disc grew slowly even in the presence of high (20%) FBS. Cells usually required up to a month from initiation of explants until P1 cultures could be established. Doubling time in the presence of 10% FBS was 6.2 days; in 20% FBS, 3.4 days, and in 25% FBS, 3.5 days. Cell viability, determined by trypan blue exclusion, averaged 96% on monolayer culture. A phase-contrast photomicrograph of cells growing out from a disc explant fragment onto a nylon mesh (X130) is shown in FIG. 2A. In FIG. 2B there is shown a scanning electron micrograph of cells spreading and extending processes onto the mesh.

When primary cultures showed a confluent outgrowth of cells from the nylon mesh, cultures were trypsinized (1:250, trypsin (0.5 g/l), EDTA (0.2 g/l)) (Irvine Scientific, Santa Ana, Calif.) and a split ration of 1:4 used for further culturing.

EXAMPLE 2

In this example, primary cell cultures were grown in alginate. Cells established in monolayer primary culture were seeded either into alginate layers on inserts (P1 cultures) or continued as monolayer P1 cultures which were subsequently split and used as the cell source for sequential P2, P3 or P4 passages seeded into alginate. Several cryofrozen cultures were thawed and expanded as P1 passages on monolayer with subsequent P2 and later passages seeded into alginate.

The alginate solution was prepared from a 1.2% solution of KELTONE LV alginate (KELCO, San Diego, Calif.) in 0.9% physiological saline with stirring for one hour. The alginate solution was sterilized by filtering through a 0.2 $\mu$m bottle top filter fitted onto a 100 ml sterile bottle.

Trypsinized primary cell cultures were assayed for cell viability and the required volume of cell suspension centrifuged at 500 rpm for five minutes in an IEC MP4R centrifuge and the medium subsequently aspirated off. An appropriate volume of sterile 1.2% KELTONE LV alginate solution was added to attain the desired cell/alginate suspension. Cells were mixed in the alginate by gentle thorough pipetting.

COSTAR TRANSWELL Clear Inserts (COSTAR, Cambridge, Mass.) were placed in multiwell plates, and the desired amount of alginate/cell suspension was carefully added to the bottom of the insert well without formation of air bubbles. A correctly prepared insert showed a fully covered filter with a meniscus formed in the insert. For a 24 well plate 50 $\mu$L of alginate/cell suspension was added to each insert. After the alginate/cell suspension was in place, each insert was carefully lifted with sterile forceps and the desired volume of 102 mM $CaCl_2$ polymerizing solution was added to the well. This volume covered the bottom of the filter, but was not enough to allow the $CaCl_2$ solution to enter into the insert. The inserts were incubated in $CaCl_2$ polymerizing solution for four minutes and the solution aspirated out. Wells were rinsed with MEM with 20% FBS (2.5 mL/well for 24 well plates).

The rinsing volume filled both well and insert, was allowed to stand for one minute, and was aspirated off. Four inserts were set up for each concentration at each time point (Days 6, 8 and 10). Each well was fed with MEM supplemented with TGF-β1l) (SIGMA) at the following doses: control (no TGF-β1), 0.25, 0.50, 1.0, 2.5, and 5 ng/ml. These alginate cultures were grown for ten days with feeding three times per week. Cell proliferation data, expressed as total [$^3$H]thymidine uptake/$\mu$g DNA, were obtained on days 6, 8, and 10.

The cells were removed from the alginate by rinsing the wells twice with 0.15M $NaCl_2$ (2.5 mL/well for 24 well plates) by lifting the insert and pipetting into the well. The rinse solution was incubated for one minute, and was aspirated off via the solution under the insert. The solution within the insert was not aspirated off. After the second rinse, the remaining liquid from the insert was wicked off by gently touching a twisted sterile gauze square to the side of the tipped well. Three times the volume of the alginate in dissolving buffer (55 mM sodium citrate and 0.15M $NaCl_2$) was added to the inside of the insert and plates incubated at 37° C. for ten minutes with shaking. Contents of the insert were gently pipetted to ensure complete dissolution of the alginate.

Figure 3A:
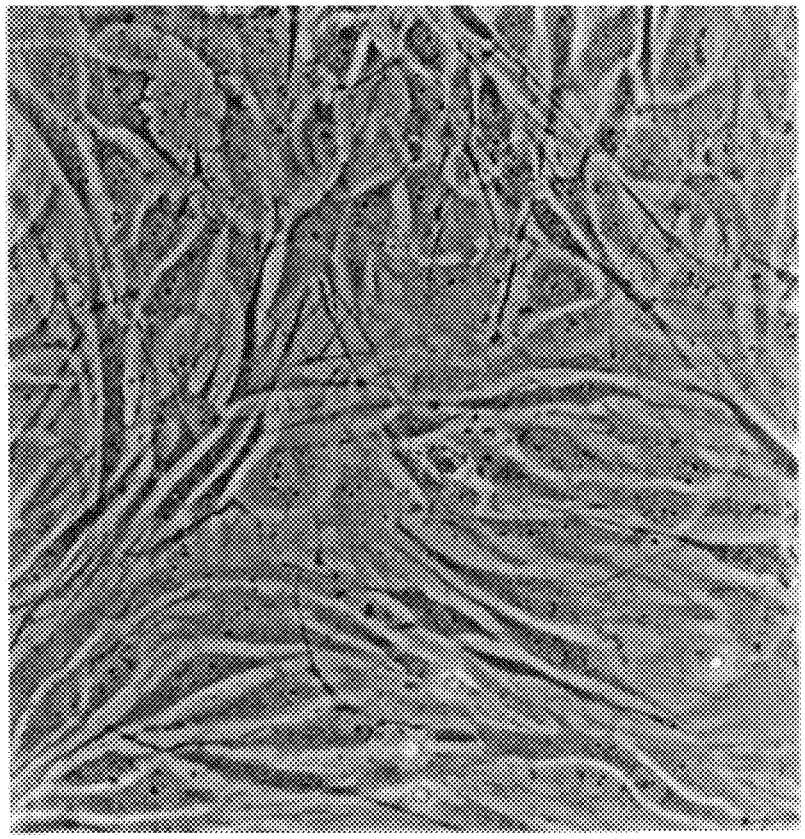
FIG. 3A shows cells grown in a three-dimensional environment.
Figure 3B:
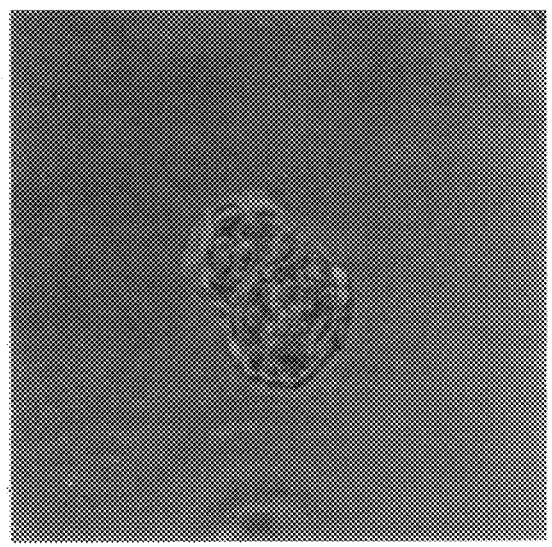
FIG. 3B is an electron microscopic examination of matrix material.

At the end of ten days, medium was withdrawn and cultures fixed with 1% neutral buffered formalin for five minutes, the insert carefully cut from the plastic holder and wrapped gently in lens paper, placed in a tissue cassette in 70% ethanol and processed using the short cycle run on a paraffin processor (Shandon Lipshaw Hypercenter XP, Pittsburgh, Pa.). Morphologic studies of cells grown in these three-dimensional microenvironments show that cells lay in a lacunar space with matrix deposited between and around the disc cells (FIG. 3A). Electron microscopic examination revealed that matrix material consisted of proteoglycans and banded and non-banded collagen (FIG. 3B).

EXAMPLE 3

Adjacent sections of three-dimensional cultures from Example 2 cut en face were collected and utilized for immunohistochemical localization of rabbit anti-human collagen Type I or rabbit anti-human collagen Type II (Biodesign International, Kennebunk, Me.), monoclonal anti-proteoglycan delta DI-4S (ICN, Costa Mesa, Calif.) or monoclonal anti-keratin sulfate (Seikagaku Corp., Tokyo, Japan).

Figure 5A:
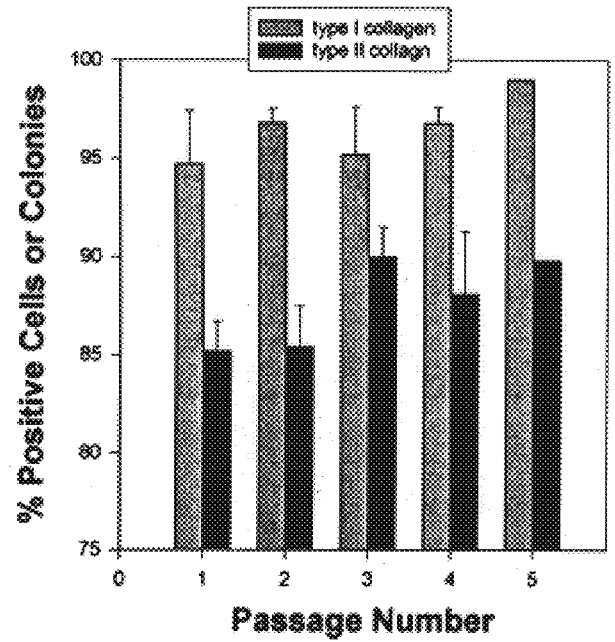
FIG. 5A presents pooled data for Type I collagen and Type II collagen.
Figure 5B:
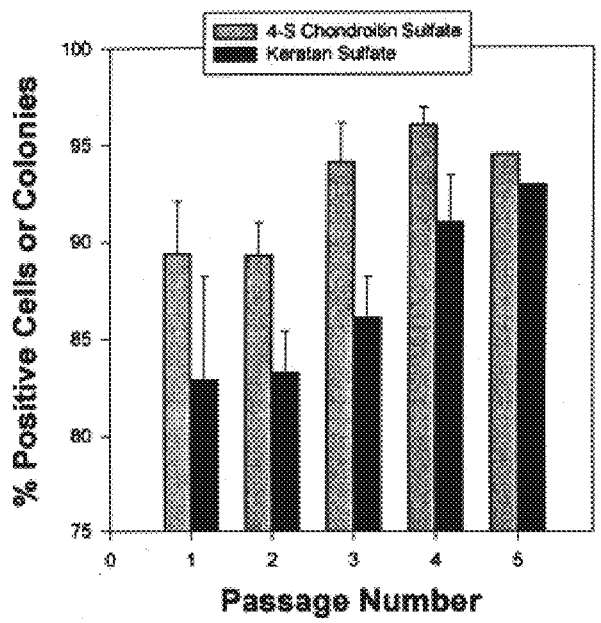
FIG. 5B presents pooled data for 4-S chondroitin sulfate and keratin sulfate.

Negative controls were incubated minus primary antibodies. Localization utilized DAB colorimetric visualization of extracellular matrix constituents. Cells or colonies were scored for positive immunohistochemical localizations using a Nikon microscope (20X objective) and OSTEOMEASURE computer software (OsteoMetrics, Inc., Atlanta, Ga.). The mean number of cells or colonies assessed for each localization was: Type I collagen: 272; Type II collagen: 260; proteoglycan delta DI-4S, 241, and keratin sulfate, 201. Nine surgical and two normal series of cells were studied in this experiment. Passages 1 through 4 were evaluated for cells from one specimen and one normal; passage number 3 was studies for normal; passages 1 through 3 for two specimens; passages 2 through 3 from three specimens; passages 2 through 4 in one, and passages 2 through 5 in two specimens. FIGS. 5A and 5B show the proportion of colonies positive for the presence of Type I or Type II collagen, 4–5 chondroitin sulfate or keratin sulfate.

Statistical Analysis

Data are presented as mean ±s.e.m. SAS® (version 6.11, SAS Institute, Inc., Cary, N.C.) software was utilized for data analysis. Standard statistical methods were employed. Paired t-test were used to compare means of frozen and non-frozen matrix scoring. To detect potential bias between frozen and non-frozen groups with respect to both passage 2 and passage 3 results (examined separately), unpaired t-tests were used. A repeated measures analysis of variance was performed to test for differences over time (passages 2, 3 and 4). All tests were two-sided, and p-values <0.05 were considered statistically significant.

Figure 4:
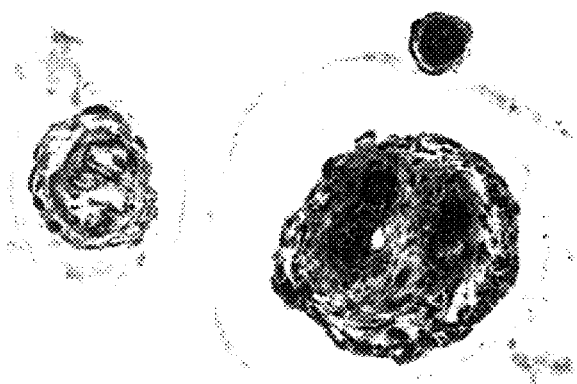
FIG. 4 is a photomicrograph of immunohistochemical localization of extracellular matrix products around first passage cells grown in agarose from a 24-year old normal subject.
Figure 4:
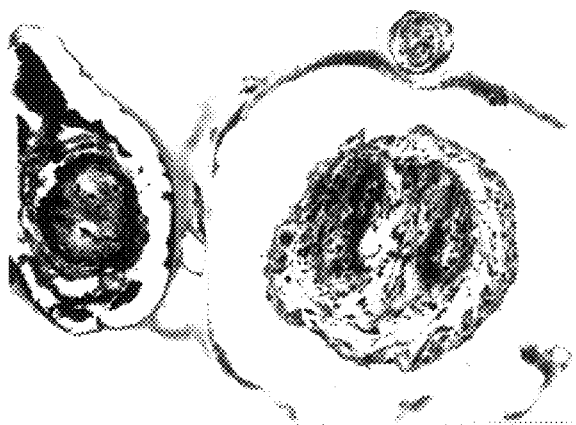
Figure 4:
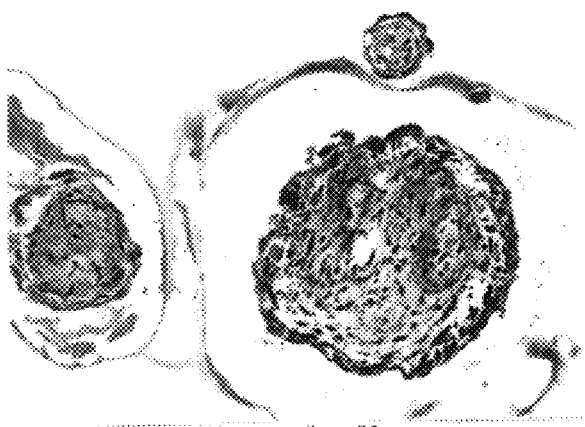
Figure 4:
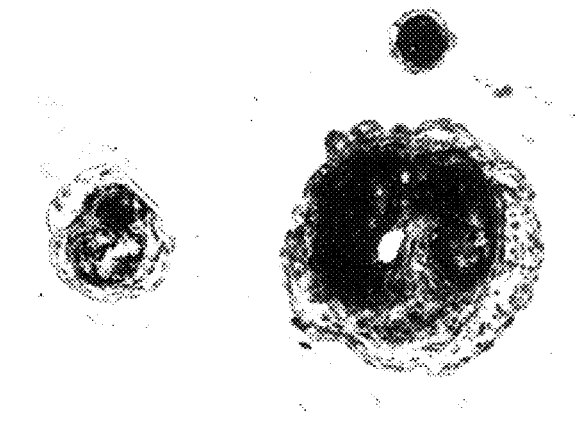
Figure 4:
Figure 4:
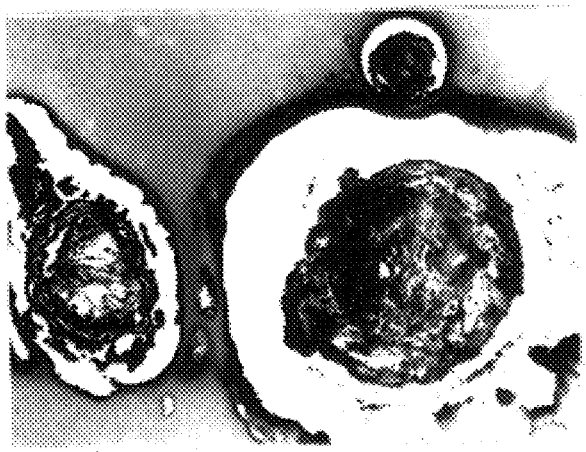

Immunohistochemical Characterization of Cells Grown in Alginate and Quantitative Scoring of Matrix in Cells and Colonies Cells from the annulus were characterized using sequential passages of cells seeded into alginate over passages 1 through 5. Representative micrographs showing localization of Type I or Type II collagen or proteoglycan D1-4S or keratin sulfate are shown in FIG. 4. The micrographs illustrated in FIG. 4 show sequential serial sections with localizations of types I, II, III, and VI collagen, 4-S-chondroitin sulfate, and keratin sulfate. Positive immunoreactivity is shown by dark staining DAB reaction product (X100).

As shown in Table 1, both non-frozen and cryo-frozen cells have been analyzed in the present study. Table 1 presents data which were analyzed by paired t-tests since the same cultures were followed through sequential passages. There were no statistically significant differences in the mean percentages of frozen and non-frozen cells with respect to the various extracellular matrix components.

TABLE 1

Summary of Quantitative Cell/Colony Scoring of Immunolocalized Extracellular Matrix Components in Non-Frozen and Frozen Cultures*

|  | Passage 1 | Passage 2** | Passage 3*** |
|---|---|---|---|
| Non-Frozen Cultures: | | | |
| Type I Collagen (n = 4) | 94.7 ± 2.7 | 96.3 ± 1.2 | 97.3 ± 1.0 |
| Type II Collagen (n = 4) | 85.3 ± 1.6 | 82.5 ± 4.0 | 86.6 ± 1.6 |
| Proteoglycan delta DI-4S (n = 4) | 89.4 ± 2.8 | 85.5 ± 1.6 | 93.8 ± 4.3 |
| Keratin sulfate (n = 4) | 82.9 ± 5.3 | 84.8 ± 2.1 | 86.0 ± 3.3 |
| Frozen Cultures: | | | |
| Type I Collagen | — | 93.3 ± 1.0 | 94.0 ± 3.8 |
| Type II Collagen | — | 87.5 ± 2.2 | 92.0 ± 2.0 |
| Proteoglycan delta DI-4S | — | 91.9 ± 2.2 | 94.4 ± 2.3 |
| Keratin sulfate | — | 82.4 ± 3.3 | 86.2 ± 2.9 |

*Data are mean % ± s.e.m. The total number of colonies or cells scored in each analysis ranged from 201 to 272.
**n = 6 for P2 for frozen cultures
***n = 7 for P3 for frozen cultures FIG. 5 presents pooled data for frozen and non-frozen cells studied from passages 1 through 5. These data were also evaluated using paired t-tests of passages 2 and 3 and of 2 and 4, respectively. There were no statistically significant differences between the mean of passage 2 and those of both passage 3 and 4, with respect to Type I collagen, Type II collagen and keratin sulfate. Passage 3 was found to have a significantly higher (p=0.02) mean incidence of proteoglycan D1-4S than did passage 2.

A repeated measures analysis of variance was also applied to the data in FIG. 5 which used five observations (data for all of passages 2, 3 and 4). No statistically significant changes over the course of passages 2, 3 or 4 were identified for the incidence of the four extracellular matrix components studied.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for propagating human intervertebral disc cells in vitro comprising:
   a) providing human intervertebral disc tissue;
   b) mincing said human intervertebral disc tissue to obtain a minced explant comprising human intervertebral disc cells; and
   c) culturing said minced explant under conditions to propagate and form a monolayer of human intervertebral disc cells, wherein the human intervertebral disc cells of said monolayer can be isolated and further propagated upon passaging.

2. The method of claim 1, wherein said minced explant is anchored by a plastic mesh.

3. A human intervertebral disc cell culture obtained by the method of claim 2 comprising a monolayer of human intervertebral disc cells and a human intervertebral disc minced explant, wherein at least a portion of said monolayer of human intervertebral disc cells is attached to said human intervertebral disc minced explant.

4. The method of claim 1 wherein said minced explant is cultured in the presence of serum, growth factors or cytokines.

5. The method of claim 4 wherein said minced explant is cultured in the presence of fetal bovine serum.

6. The method of claim 4 wherein said minced explant is cultured in the presence of transforming growth factor beta (TGF-β).

7. A human intervertebral disc cell culture obtained by the method of claim 1 comprising a monolayer of human intervertebral disc cells and a human intervertebral disc minced explant, wherein at least a portion of said monolayer of human intervertebral disc cells is attached to said human intervertebral disc minced explant.

8. A method for culturing human intervertebral disc cells in a three-dimensional structure in vitro comprising:
   a) providing human intervertebral disc tissue;
   b) mincing said human intervertebral disc tissue to obtain a minced explant comprising human intervertebral disc cells;
   c) culturing said minced explant under conditions to propagate and form a monolayer of human intervertebral disc cells, wherein the human intervertebral disc cells of said monolayer can be isolated and further propagated upon passaging;
   d) isolating said human intervertebral disc cells from said monolayer;
   e) seeding the isolated cells into a carrier such that the isolated cells are dispersed and distributed in the carrier thereby forming a three-dimensional structure; and
   f) culturing said dispersed and distributed cells in the three-dimensional structure.

9. The method of claim 8, wherein said three-dimensional structure is formed in a cell well insert.

10. The method of claim 8, wherein said carrier is alginate.

11. The method of claim 8, wherein said carrier is agarose.

* * * * *